United States Patent
Martín Del Campo López et al.

(10) Patent No.: US 10,517,906 B2
(45) Date of Patent: Dec. 31, 2019

(54) GELATINOUS MIXTURE OF PROBIOTICS AND PREBIOTICS WITH SYNERGIC SYMBIOTIC ACTION FOR TREATING CHRONIC RENAL DISEASE

(71) Applicant: NUTRIMENTOS INTELIGENTES, S.A. DE C.V., Guadalajara, Jalisco (MX)

(72) Inventors: Fabiola Martín Del Campo López, Guadalajara (MX); Luis Gerardo Gonzalez Delgado, Guadalajara (MX); Daniela Viramontes Horner, Guadalajara (MX); Guillermo García García, Guadalajara (MX); Julio Alberto Ramos De La Mora, Guadalajara (MX)

(73) Assignee: NUTRIMENTOS INTELIGENTES, S.A. DE C.V., Guadalajara (MX)

( * ) Notice: Subject to any disclaimer, the term of this patent is extended or adjusted under 35 U.S.C. 154(b) by 418 days.

(21) Appl. No.: 14/774,234

(22) PCT Filed: Apr. 2, 2013

(86) PCT No.: PCT/MX2013/000041
§ 371 (c)(1),
(2) Date: Sep. 10, 2015

(87) PCT Pub. No.: WO2014/148881
PCT Pub. Date: Sep. 25, 2014

(65) Prior Publication Data
US 2016/0051600 A1 Feb. 25, 2016

(30) Foreign Application Priority Data
Mar. 21, 2013 (MX) .................. MX/a/2013/003216

(51) Int. Cl.
*A01N 63/00* (2006.01)
*A61K 35/745* (2015.01)
(Continued)

(52) U.S. Cl.
CPC .......... *A61K 35/745* (2013.01); *A23L 33/135* (2016.08); *A61K 9/0056* (2013.01);
(Continued)

(58) Field of Classification Search
None
See application file for complete search history.

(56) References Cited

U.S. PATENT DOCUMENTS

| | | |
|---|---|---|
| 2004/0106185 A1 | 6/2004 | Ranganathan |
| 2004/0197352 A1 | 10/2004 | Ranganathan |
| 2012/0308525 A1* | 12/2012 | Greenberg ............. A23L 33/40 424/93.4 |

FOREIGN PATENT DOCUMENTS

| | | |
|---|---|---|
| ES | 2198073 T3 | 1/2004 |
| JP | 2004/008165 A | 1/2004 |
| WO | WO 2013/045724 A1 | 4/2013 |

OTHER PUBLICATIONS

International Search Report, dated Jul. 15, 2013, from International Phase of the instant application.

* cited by examiner

*Primary Examiner* — Eric M. Bowers
(74) *Attorney, Agent, or Firm* — Steven M. Greenberg, Esq.; Shutts & Bowen LLP

(57) ABSTRACT

The invention relates to the fields of application of health, biotechnology and nutrition, the aim of the invention being to provide a gelatinous mixture of probiotics and prebiotics with synergic symbiotic action for the treatment of chronic renal disease, the characteristics and components thereof reducing the concentration of uremic toxins, improving the (Continued)

renal function of the patient with an increase in urea, creatinine, uric acid, p-cresols or indoles in the blood. The gelatinous mixture of probiotics and prebiotics with synergic symbiotic action for the treatment of chronic renal disease is easier to administrate orally as it does not require the consumption of liquids for the administration thereof, reducing liquid retention. Another advantage of the present invention is the fact that it refers to live and active bacteria. The present invention is also used a primary source of food with known prebiotic effects, an element which is not considered in other inventions; it is not in a pharmaceutical form. The probiotic bacteria are found "live and active" and in "synergic action" with the prebiotic fibers of plant origin such as "blue agave fructans (blue agave inulin)".

5 Claims, 2 Drawing Sheets

(51) Int. Cl.
*A61K 9/00* (2006.01)
*A61K 47/42* (2017.01)
*A61K 35/741* (2015.01)
*A61K 35/747* (2015.01)
*A61K 36/88* (2006.01)
*A61K 31/702* (2006.01)
*A61K 31/733* (2006.01)
*A61K 36/55* (2006.01)
*A61K 36/752* (2006.01)
*A61K 36/28* (2006.01)
*A23L 33/135* (2016.01)
*A61K 35/00* (2006.01)

(52) U.S. Cl.
CPC .......... *A61K 9/0095* (2013.01); *A61K 31/702* (2013.01); *A61K 31/733* (2013.01); *A61K 35/741* (2013.01); *A61K 35/747* (2013.01); *A61K 36/28* (2013.01); *A61K 36/55* (2013.01); *A61K 36/752* (2013.01); *A61K 36/88* (2013.01); *A61K 47/42* (2013.01); *A23V 2002/00* (2013.01); *A61K 2035/115* (2013.01)

GELATINOUS MIXTURE OF PROBIOTICS AND PREBIOTICS WITH SYNERGIC SYMBIOTIC ACTION FOR TREATING CHRONIC RENAL DISEASE

TECHNICAL FIELD OF THE INVENTION

The present invention relates to the field of application in the health, biotechnology and nutrition sectors, since its object is to provide a gelatinous mixture of probiotics and prebiotics with synergic symbiotic action for treating chronic renal disease, because thanks to its characteristics and components, it reduces the concentration of uremic toxins, improving the renal function of a patient who has elevated urea, creatinine, uric acid, p-cresols or indoles in the blood.

PRIOR ART

In 2008, the USRDS published that chronic renal disease (CRD) is a serious public health problem around the world, whose prevalence and incidence continue to grow. CRD in the terminal stage is associated with an elevated risk of morbidity, mortality, poor quality of life, as well as high costs for its treatment.

The accumulation of products derived from the body's metabolism, such as urea, creatinine, uric acid, phosphates, indoles, phenols, among others, gives rise to what we know as uremia (retention of uremic toxins), and this in turn is the cause of the signs and symptoms of the patient. Therefore, one of the primary objectives of the treatment of CRD patients is to reduce the accumulation of nitrogenated products and uremic toxins, since they are known to have a negative effect on the renal and cardiovascular function of patients.

In the patient with CRD, the elimination of toxins by the kidney is reduced, so that the concentration of toxins in the blood rapidly increases. The uremic toxins come from the actual internal metabolism of the body, as well as from production in the intestine; in fact, the intestine is one of the principal regulators of the production of these toxins. On the intestinal level, the toxins can come directly from foods or they can be generated by the metabolism of certain bacteria which are found in the intestine (Schepers, 2010). Therefore, the strategies aimed at promoting the elimination of toxins by the fecal route is an excellent option for improving the quality of life and maintaining the renal function of patients with advanced CRD. The administration of certain probiotic bacteria, as well as prebiotic fiber, has been demonstrated to be able to reduce the concentrations of toxins in the patient with CRD (Schepers, 2010).

In the prior art, there are various patents for treating CRD, such as U.S. Pat. No. 6,706,263 B2, entitled "Compositions and methods for alleviating symptoms of uremia in patients"*, which describes microencapsulated and/or enteric compounds which contain a mixture of sorbents with special affinity for uremic toxins, as well as a source of bacteria with ability to metabolize urea and ammonia. In addition, it describes methods for using these compounds to alleviate the symptoms of uremia. This patent also has the drawback of the composition being in pharmaceutical form (microencapsulated and with an enteric coating), which needs to be administered with some liquid.

* sic; The title is: "Composition for alleviating symptoms of uremia in patients."—Translator's note.

U.S. Pat. No. 6,706,287 B2 entitled "Prebiotic and probiotic compositions and methods for their use in gut-based therapies" proposes microencapsulated and/or enteric compounds which contain a mixture of probiotics, prebiotics and ammoniophilic bacteria with high urease activity, with or without specific sorbents for uremic toxins. As well as methods for alleviating the symptoms of uremia by administering this composition. Nevertheless, the compounds are again in pharmaceutical form (microencapsulated and with an enteric coating), which need to be administered with some liquid.

Another patent dealing with the treatment of CRD is U.S. Pat. No. 7,026,160 B2, "Oral bacteriotherapy compositions and methods", which describes a compound for the treatment of kidney failure with bacteria able to convert nitrogen wastes into nontoxic components. It advocates the bacteria *Bacillus pasteurii* with enteric coating. One of the main drawbacks of this patent is that the compound is present in pharmaceutical form (enteric coating), which need to be administered with some liquid. Moreover, this invention does not utilize a combination with some other nutritional element, such as vitamins or prebiotics.

The present invention intends to improve the drawbacks of the above-cited inventions, in that it relates to a gelatinous mixture of probiotics and prebiotics with synergic symbiotic action for treating chronic renal disease, making its administration via oral route simpler, as well as reducing the need to consume liquids for its administration, considering that a major problem of patients with renal disease is fluid retention, which makes it necessary to restrict fluids. Another benefit of the present invention is the fact that it deals with active and live bacteria in comparison to the prior inventions, which require them to be lyophilized for the process of microencapsulation and enteric coating. The present invention furthermore uses inulin as the primary source of nutrition with known prebiotic effects; inulin is an element not considered in the prior art. The present invention uses a mixture of prebiotics and probiotics with other nutrients having symbiotic and synergic actions, and furthermore it is not present in pharmaceutical form. The probiotic bacteria are "active and live" and in "synergic action" with the prebiotics, which are fiber of plant origin.

There are inventions related to gelatinous mixtures of probiotics and prebiotics with symbiotic synergic action, such as the international application WO 2010/059022 A1, which describes a method of obtaining a mixture of probiotics, prebiotics and nutrients with symbiotic synergic action for the development of functional foods, basically utilizing inulin as the prebiotic nutrient and a mixture of at least one strain of lactobacilli, bifidobacteria, streptococci or yeast as source of probiotics. Likewise, U.S. Pat. No. 8,287,929 B2 describes a protein gelatinous food and its manufacture process, said gelatinous food being meant to improve human digestion and maximize the utilization of the food ingested by way of restoring the intestinal flora. Nevertheless, the two aforementioned inventions are addressed to the method of production of the protein gel for the purpose of restoring the human intestinal flora. The present invention is a gelatinous mixture of probiotics and prebiotics with synergic symbiotic action for treating chronic renal disease which permits reducing uremic toxins and improving the renal function in patients with advanced chronic renal disease.

DETAILED DESCRIPTION OF THE INVENTION

The characteristic details of the gelatinous mixture of probiotics and prebiotics with synergic symbiotic action for treating chronic renal disease are shown clearly in the following description and in the accompanying figures, with illustrative and non-limiting character:

Figure 1:
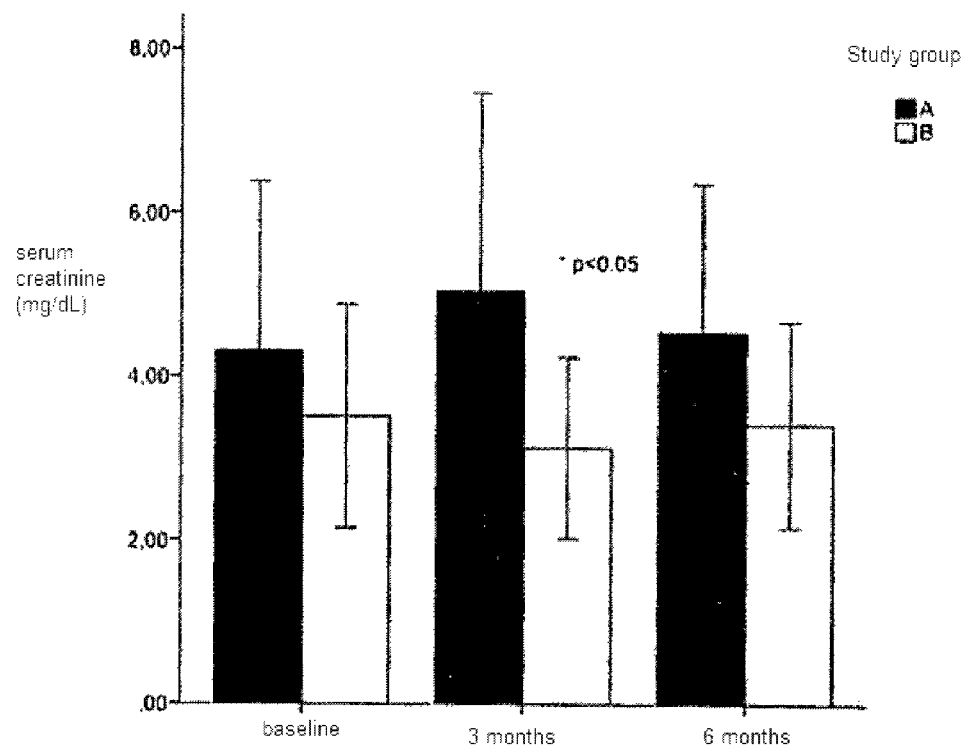
FIG. 1 shows a graph evaluating the effect of administering the gelatinous mixture of probiotics and prebiotics with synergic symbiotic action for treating chronic renal disease for 6 months, as compared to the administration of a placebo with the same characteristics of taste, color and texture, on the concentrations of creatinine in patients with advanced kidney failure.

The present invention relates to a gelatinous mixture of probiotics and prebiotics with synergic symbiotic action for treating chronic renal disease, said mixture being composed of:
1.976 to 2.964 liters of water;
703.375 to 951.625 grams of cane sugar;
1015.83 to 1422.167 grams of glucose in the liquid state;
195.5 to 264.5 grams of protein element;
41.85 to 51.15 grams of xanthan gum;
112 to 168 grams of prebiotic fiber of plant origin;
30 to 35 grams of vitamins;
1 gram of citrus seed extract;
44.62 to 60.37 grams of citric acid;
9 to 11 grams of malic acid;
4.875 to 5.850 grams of bifidobacteria;
1.625 to 1950 grams of lactobacilli;
3.325 to 3675 milliliters of colorant, which is a mixture of fine powdered pigment with water; and
9 to 10 grams of fragrance.

Where the protein element is a mixture of 30% glycerin, 14% proline, 8% hydroxyproline, 45% other amino acids, 1.2% water and 1.8% mineral salts; where the last two items must not contain fats or carbohydrates.

Flax fiber is composed of 40.9% polysaturated fats which contain alpha-linoleic acid, 20% protein of plant origin, 28% vegetable fiber, 7.7% moisture content and 3.4% mineral residue.

It is essential that the combined concentration of bifidobacteria and lactobacilli is at least $150 \times 10^9$ CFU (colony forming units) per gram. This permits $2 \times 10^9$ CFU in portions of 15 grams of finished product. The probiotics must be added to the lyophilized mixture. The portion should be maintained in a ratio of 2:1 to 3:1 of bifidobacteria to lactobacilli, respectively. This proportion produces a combined action where the lactobacilli condition the digestive environment to facilitate the activity of the bifidobacteria and thus achieve an optimal absorption of proteins and nutrients, providing a benefit to the human body, namely: the decrease in uremic toxins and improved renal function in patients with advanced chronic renal disease, with elevated urea, creatinine, uric acid, p-cresols or indoles in the blood. The prebiotic fiber of plant origin can be fructo-oligosaccharides, flax, fructans of Blue Agave Tequiliana Weber, or chicory inulin.

With the above-described gelatinous mixture of probiotics and prebiotics with synergic symbiotic action for treating chronic renal disease one prepares a food, such as a cake, a gel, a beverage or any other edible product for humans, in order to decrease uremic toxins and improve the renal function in patients with advanced chronic renal disease, with elevated urea, creatinine, uric acid, p-cresols or indoles in the blood.

An experimental research study was conducted with patients having advanced kidney failure for 6 months; the subjects were randomized into two treatment groups: the group designated B was administered the gelatinous mixture of probiotics and prebiotics with synergic symbiotic action for treating chronic renal disease, and the group A was administered a placebo with the same characteristics of taste, color and texture. Both groups received the standard medical treatment and specialized nutritional follow-up. The gelatinous mixture of probiotics and prebiotics with synergic symbiotic action for treating chronic renal disease and the placebo were administered in similar fashion in a dose of two packets of product on a fasting stomach every day for 6 months.

Results of the Tests

The following table shows the effect of administering the gelatinous mixture of probiotics and prebiotics with synergic symbiotic action for treating chronic renal disease for 6 months, as compared to administering a placebo with the same characteristics of taste, color and texture on the variables of renal function and concentration of toxins in patients with advanced kidney failure. One notices that the levels of urea, creatinine, proteinuria and phosphorus are lower in group B, which is the one given the gelatinous mixture of probiotics and prebiotics with synergic symbiotic action for treating chronic renal disease; and the renal function measured by the CKD-EPI (Chronic Kidney Disease-Epidemiological Collaboration) formula and with the MDRD (modification of diet in renal disease) formula is higher in group B than in group A. In conclusion, group B had a better preservation of renal function than group A for the 6 months of treatment.

| Variable | Baseline | | 3 months | | 6 months | |
|---|---|---|---|---|---|---|
| | A<br>n = 21 | B<br>n = 14 | A<br>n = 16 | B<br>n = 13 | A<br>n = 11 | B<br>n = 12 |
| Urea (mg/dL) | 137.5 ± 57.2 | 134.1 ± 47.6 | 144.7 ± 52.6 | 134.3 ± 42.2 | 140 ± 33 | 152 ± 40 |
| Creatinine (mg/dL) | 4.3 ± 2.0 | 3.5 ± 1.3 | 5.0 ± 2.4 | 3.1 ± 1.1* | 4.5 ± 1.8 | 3.4 ± 1.2 |
| Glomerular filtration rate, CKD-EPI (mL/min) | 16.7 ± 8.8 | 17.5 ± 6.5 | 13.6 ± 7.3 | 19.7 ± 6.5* | 14.6 ± 7.3 | 18.6 ± 8.1 |

|  | Baseline | | 3 months Variable | | 6 months | |
| --- | --- | --- | --- | --- | --- | --- |
|  | A n = 21 | B n = 14 | A n = 16 | B n = 13 | A n = 11 | B n = 12 |
| MDRD (mL/min) | 17.5 ± 9.2 | 18.3 ± 6.5 | 14.3 ± 7.5 | 20.4 ± 6.3* | 15.4 ± 7.5 | 19.3 ± 7.9 |
| Proteinuria (mg/24 h) | 1287 (322-4510) | 786 (412-1674) | 2088 (934-3074) | 849 (268-1413)* | 1043 (833-2810) | 531 (154-1573) |
| Phosphorus (mg/dL) | 4.6 ± 0.9 | 4.6 ± 0.4 | 4.5 ± 1.1 | 4.0 ± 0.6+ | 4.3 ± 0.5 | 4.4 ± 0.6^ |

Said effect of the decrease in creatinine in patients with advanced kidney failure can be clearly seen in FIG. 1.

Figure 2:
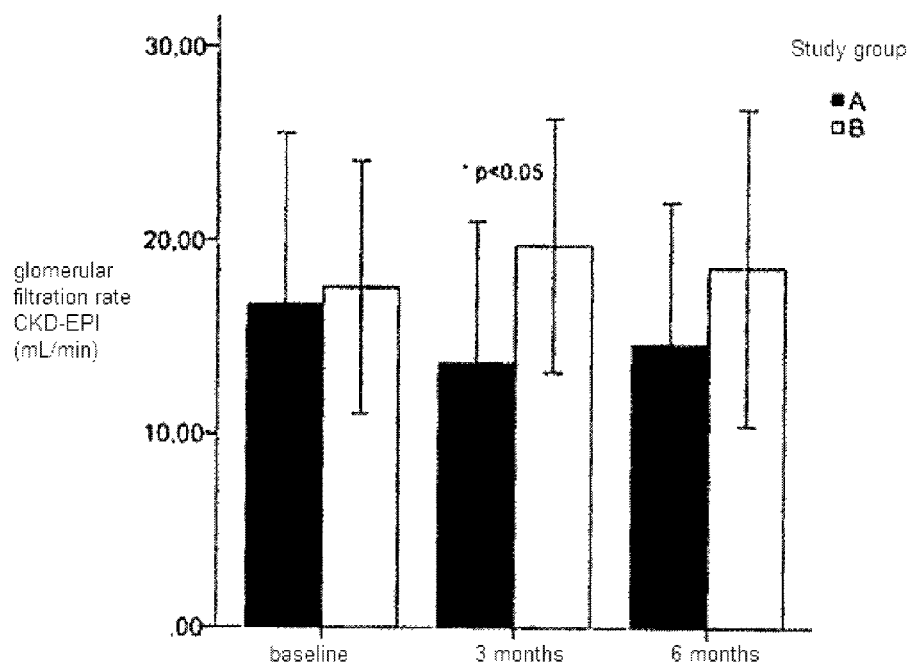
FIG. 2 shows a graph evaluating the effect of administering the gelatinous mixture of probiotics and prebiotics with synergic symbiotic action for treating chronic renal disease for 6 months, as compared to the administration of a placebo with the same characteristics of taste, color and texture, on the renal function as measured with the CKD-EPI (Chronic Kidney Disease—Epidemiological Collaboration) formula in patients with advanced kidney failure.

FIG. 2 evaluates the effect of administering the gelatinous mixture of probiotics and prebiotics with synergic symbiotic action for treating chronic renal disease for 6 months, as compared to administering a placebo with the same characteristics of taste, color and texture on renal function as measured by the CKD-EPI (Chronic Kidney Disease-Epidemiological Collaboration) formula in patients with advanced kidney failure, where one can notice that the glomerular filtration rate (mL/min) is more stable in group B.

Figure 3:
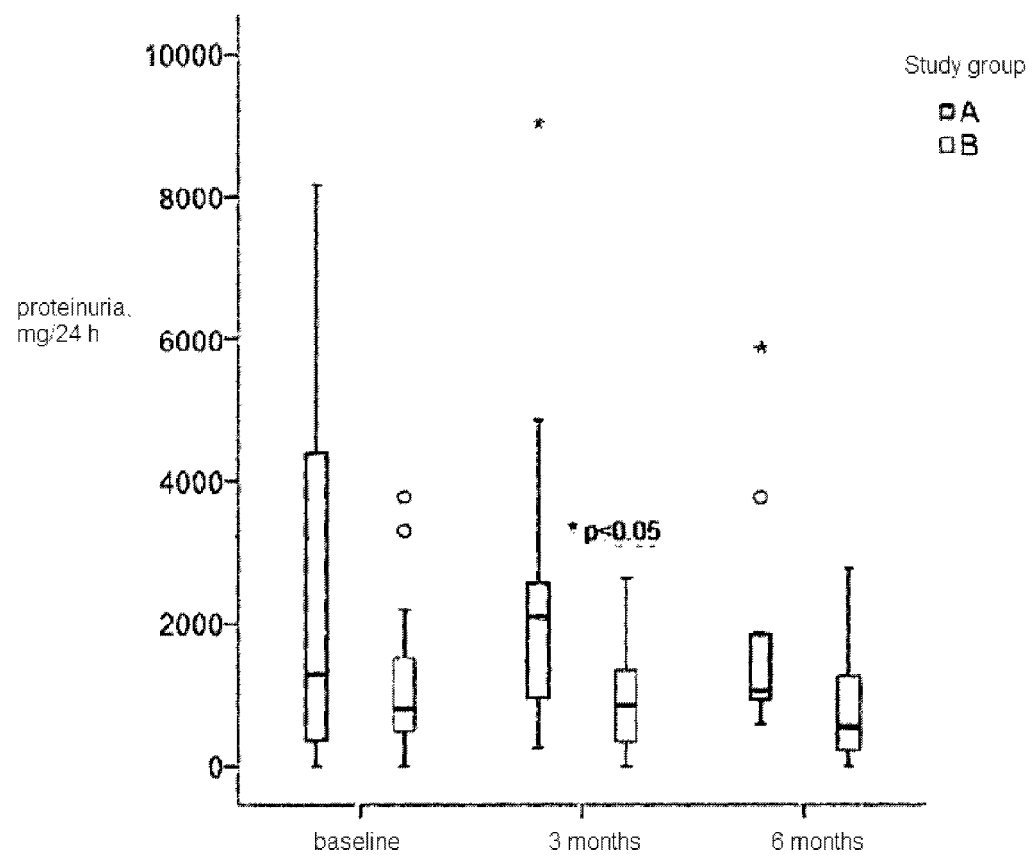
FIG. 3 shows a graph evaluating the effect of administering the gelatinous mixture of probiotics and prebiotics with synergic symbiotic action for treating chronic renal disease for 6 months, as compared to the administration of a placebo with the same characteristics of taste, color and texture, on the levels of proteinuria in patients with advanced kidney failure.

And lastly, FIG. 3 shows a graph evaluating the effect of administering the gelatinous mixture of probiotics and prebiotics with synergic symbiotic action for treating chronic renal disease for 6 months, as compared to administering a placebo with the same characteristics of taste, color and texture on the levels of proteinuria in patients with advanced kidney failure, where the average of group B is lower than group A.

The following table shows the number and percentage of patients requiring commencement of dialysis due to a greater progression or a worsening of the renal disease, where it is seen that group A had a larger number of subjects who started dialysis in comparison to group B. These data show that at 6 months follow-up the renal function values did not end up being different between the groups, since group A not only progressed more rapidly in the disease, but also the patients left the study on account of commencement of dialysis.

| Patient status | Group A | Group B | P |
| --- | --- | --- | --- |
| Alive and/or active | 16 (76%) | 13 (93%) | 0.37 |
| Began dialysis | 5 (24%) | 0 |  |
| Died | 0 | 1 (7%)* |  |

As can be seen from the table above, the patients of group B, that is, those receiving the gelatinous mixture of probiotics and prebiotics with synergic symbiotic action for treating chronic renal disease, did not require dialysis, the death recorded being because of:
 *heart arrhythmia secondary to hyperkalemia and FOM due to uremic syndrome A table is presented below showing the effect of administering the gelatinous mixture of probiotics and prebiotics with synergic symbiotic action for treating chronic renal disease at 3 and 6 months on the variables of renal function and concentration of toxins in patients with advanced kidney failure coming for treatment to a specialized kidney center, different from the tests performed with groups A and B, where one can clearly observe the reduction in urea, phosphorus and creatinine at 3 and 6 months in the patients given the gelatinous mixture of probiotics and prebiotics with synergic symbiotic action for treating chronic renal disease.

| Variable | Baseline (n = 19) | 3 months (n = 17) | 6 months (n = 7) |
| --- | --- | --- | --- |
| Uric acid (mg/dL) | 8 ± 2.6 | 7.9 ± 1.9 | 8.1 ± 4.2 |
| Urea (mg/dL) | 149 ± 66 | 147 ± 60 | 125 ± 64 |
| Phosphorus (mg/dL) | 4.5 ± 1.1 | 4.8 ± 1.4 | 4.4 ± 1 |
| Creatinine (mg/dL) | 6.3 ± 3 | 5.8 ± 2.7 | 4.4 ± 2.4 |

In the following table one can clearly observe the reduction in urea, phosphorus and creatinine at 3 and 6 months in the patients who were administered the gelatinous mixture of probiotics and prebiotics with synergic symbiotic action for treating chronic renal disease. Upon analysis of the subjects who achieved improvements in their values, 47% and 65% of the subjects decreased their concentrations of urea and creatinine, respectively, at 3 months, while 71% and 43% of the patients who continued the treatment up to 6 months achieved reductions in these same parameters.

| Variable | 3 months (n = 17) | 6 months (n = 6) |
| --- | --- | --- |
| Reduction of urea | 8 (47%) | 5 (71%) |
| Reduction of creatinine | 11 (65%) | 3 (43%) |

According to the results obtained in the tests for 6 months, it is demonstrated that the gelatinous mixture of probiotics and prebiotics with synergic symbiotic action for treating chronic renal disease is able to decrease the concentration of certain toxins, resulting in a greater maintenance of renal function of patients with advanced kidney failure.

The use of the gelatinous mixture of probiotics and prebiotics with synergic symbiotic action for treating chronic renal disease can be of great help for use as an adjuvant in the treatment of patients with renal disease, since it can decrease the concentration of toxins and maintain renal function more efficiently, postponing as long as possible the commencement of dialysis therapy. Therefore, it is concluded that the gelatinous mixture of probiotics and prebiotics with synergic symbiotic action for treating chronic renal disease can be used to prepare a food, such as a cake, a gel, a beverage, or any edible product for humans, in order to decrease uremic toxins and improve renal function in patients with advanced chronic renal disease who have elevated urea, creatinine, uric acid, p-cresols or indoles in the blood.

Having sufficiently described my invention, I consider it to be novel and therefore I claim as my exclusive property the content of the following claims:

1. A method of treating chronic renal disease comprising administering to a subject in thereof a gelatinous mixture of probiotics and prebiotics with synergic symbiotic action comprising the following ingredients:
- 1.976 to 2.964 liters of water;
- 703.375 to 951.625 grains of cane sugar;
- 1015.83 to 1422.167 grams of glucose in the liquid state;
- 195.5 to 264.5 grams of protein element;
- 41.85 to 51.15 grams of xanthan gum;
- 112 to 168 grams of fructans of blue agave (Agave tequilana Weber);
- 30 to 35 grams of vitamins;
- 1 gram of citrus seed extract;
- 44.62 to 60.37 grams of citric acid;
- 9 to 11 grams of malic acid;
- 4.875 to 5.850 grams of bifidobacteria;
- 1.625 to 1950 grams of lactobacilli;
- 3.325 to 3675 milliliters of colorant; and
- 9 to 10 grains of fragrance.

2. The method according to the claim 1, wherein the protein element is a mixture of 30% glycerin, 14% proline, 8% hydroxyproline, 45% other amino acids, 1.2% water and 1.8% mineral salts; where the last two items must not contain fats or carbohydrates.

3. The method according to claim 1, wherein the combined concentration of bifidobacteria and lactobacilli is at least $150 \times 10^9$ CFU (colony forming units) per grain.

4. The method according to claim 1, wherein the food is a gel.

5. The method according to claim 1, wherein the food is a beverage.

\* \* \* \* \*